United States Patent [19]
Kolehmainen et al.

[11] Patent Number: 5,997,487
[45] Date of Patent: Dec. 7, 1999

[54] INFUSION WIRE HAVING FIXED CORE WIRE

[75] Inventors: Donald J. Kolehmainen, Orange; Blair D. Walker, Lake Forest, both of Calif.

[73] Assignee: Micro Therapeutics, Inc., Irvine, Calif.

[21] Appl. No.: 08/900,024

[22] Filed: Jul. 24, 1997

Related U.S. Application Data

[63] Continuation-in-part of application No. 08/541,147, Oct. 11, 1995.

[51] Int. Cl.$^6$ .......................................................... A61B 5/00
[52] U.S. Cl. .............................. 600/585; 604/95; 604/280
[58] Field of Search .................................... 600/585, 433, 600/434; 604/95, 96

[56] References Cited

U.S. PATENT DOCUMENTS

| | | | |
|---|---|---|---|
| 3,841,308 | 10/1974 | Tate | 128/2 |
| 4,464,176 | 8/1984 | Wijayrathna et al. | 604/164 |
| 4,538,622 | 9/1985 | Samson et al. | 128/722 |
| 4,748,986 | 6/1988 | Morrison et al. | 128/772 |
| 4,917,104 | 4/1990 | Rebell | 128/772 |
| 4,932,419 | 6/1990 | de Toledo | 128/772 |
| 4,955,862 | 9/1990 | Sepetka | 604/164 |
| 5,174,302 | 12/1992 | Palmer | 128/772 |
| 5,178,158 | 1/1993 | de Toledo | 128/772 |
| 5,184,627 | 2/1993 | de Toledo | 128/772 |
| 5,211,636 | 5/1993 | Mische | 604/264 |
| 5,322,508 | 6/1994 | Viera | 604/52 |
| 5,376,083 | 12/1994 | Mische | 604/204 |
| 5,462,523 | 10/1995 | Samson et al. | 604/30 |
| 5,554,114 | 9/1996 | Wallace et al. | 604/53 |
| 5,569,197 | 10/1996 | Helmus et al. | 604/96 |
| 5,603,694 | 2/1997 | Brown et al. | 604/49 |
| 5,624,396 | 4/1997 | McNamara et al. | 604/93 |
| 5,626,564 | 5/1997 | Zhan et al. | 604/164 |
| 5,827,201 | 10/1998 | Samson et al. | 600/585 |

FOREIGN PATENT DOCUMENTS

WO 97/13455  4/1997  WIPO .............................. A61B 5/00

OTHER PUBLICATIONS

"Products for Regional Thrombosis" brochure of Meditech (Boston Scientific Corp.) 1992 (7 pages).

T. McNamara M.D. et al., "Coaxial system improves thrombolysis of ischemia", Diagnostic Imaging, pp. 122–131, Nov. 1991.

*Primary Examiner*—Max Hindenburg
*Assistant Examiner*—Pamela L. Wingood
*Attorney, Agent, or Firm*—Joseph F. Breimayer

[57] ABSTRACT

An infusion wire that can be used either as a guidewire or an infusion catheter having a tapered core wire within an infusion lumen formed of the aligned lumens of the conduit of a proximal connector housing, an inner sheath in a proximal infusion wire portion and a distal coil wire in a distal infusion wire portion. The inner sheath is formed either of a polyimide tube or a wire reinforced polyimide tube, at least in a proximal section thereof In a fixed core wire embodiment, the core wire proximal end is attached to the connector housing, and the core wire distal end is connected to the distal end of the distal wire coil. An outer sheath is attached to the connector housing and formed over the inner sheath and the distal wire coil. A plurality of infusion side holes are formed in a distal infusion segment of the outer sheath in fluid communication with the infusion lumen. At the junction of the inner sheath and the distal wire coil, a radiopaque wire coil of a material having a higher radiopacity than the distal wire coil is formed into a plurality of radiopaque wire coil turns of substantially the same pitch, inner lumen diameter and outer diameter as the distal wire coil. The distal wire coil is space wound with distally increasing coil spacings. The distal core wire portion extending through the distal wire oil is tapered distally either continuously or in a stepped manner.

24 Claims, 5 Drawing Sheets

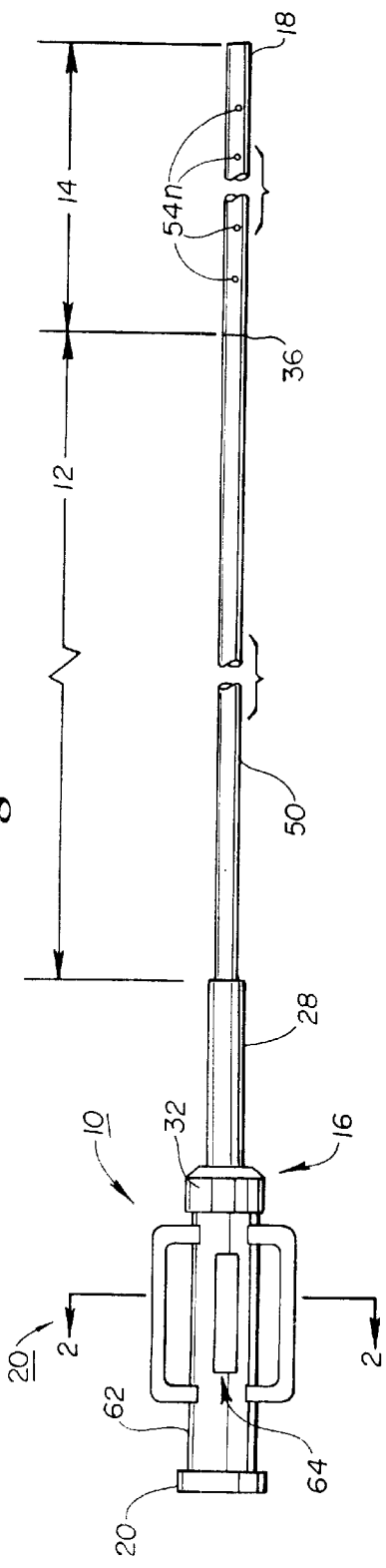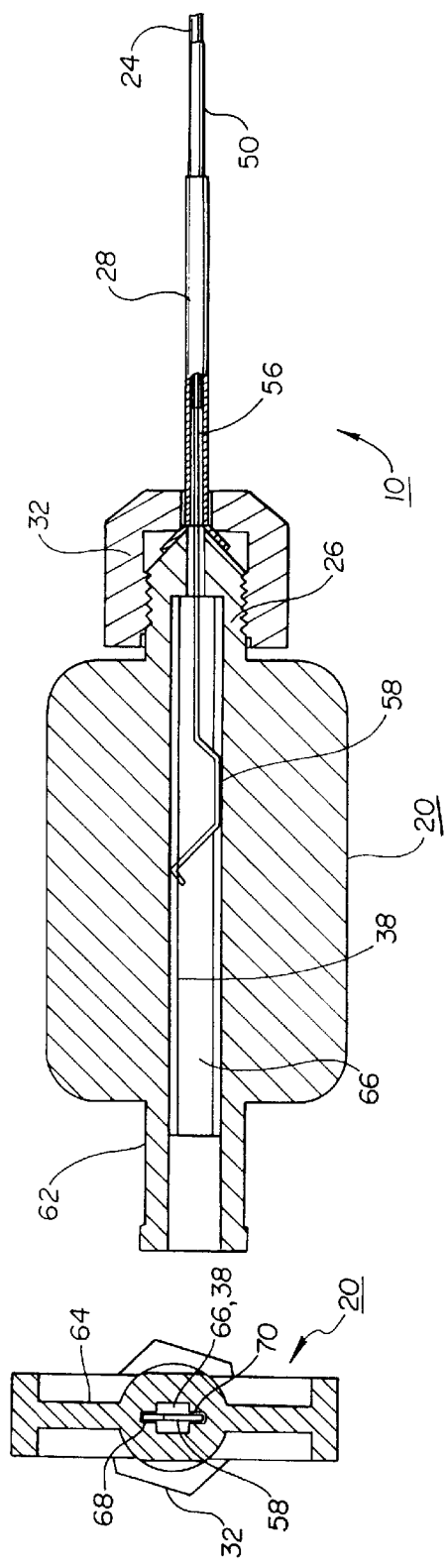

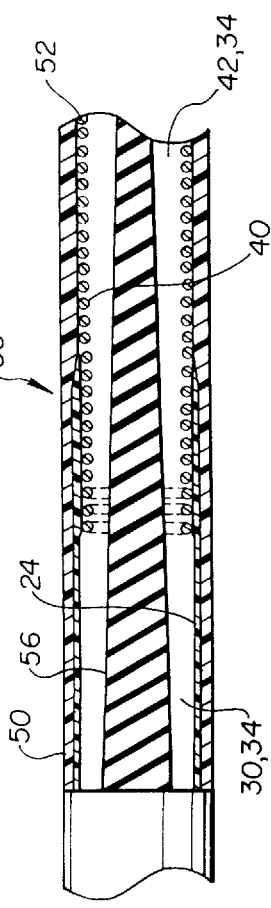
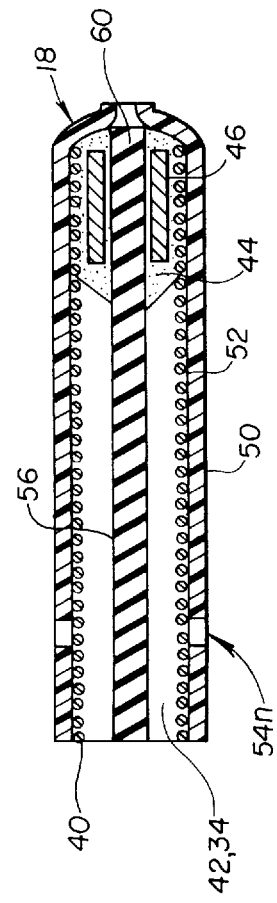
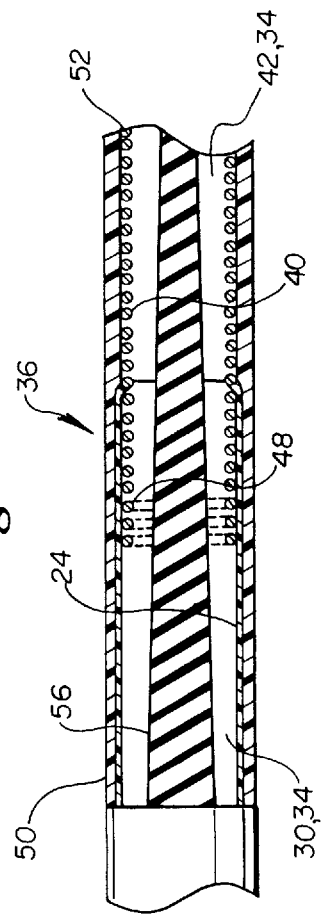

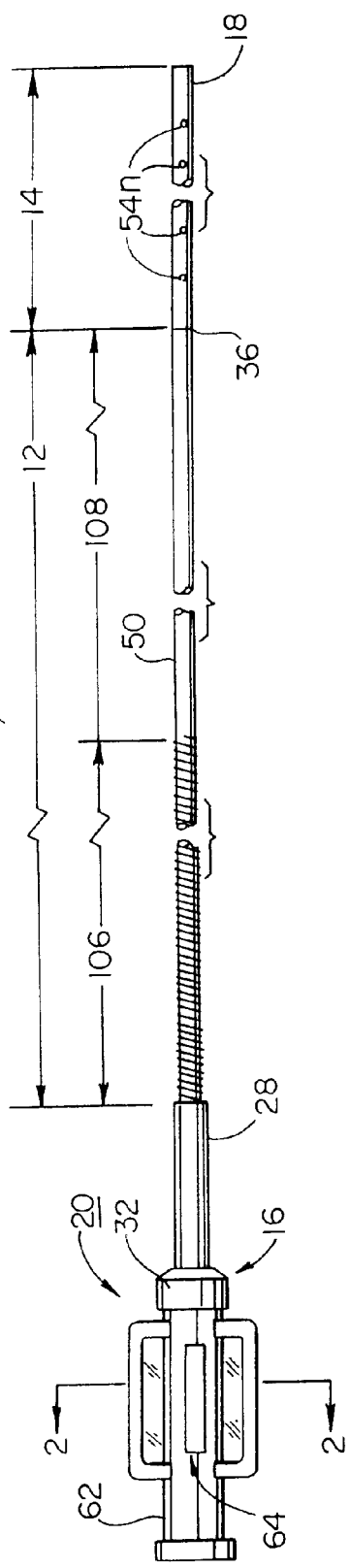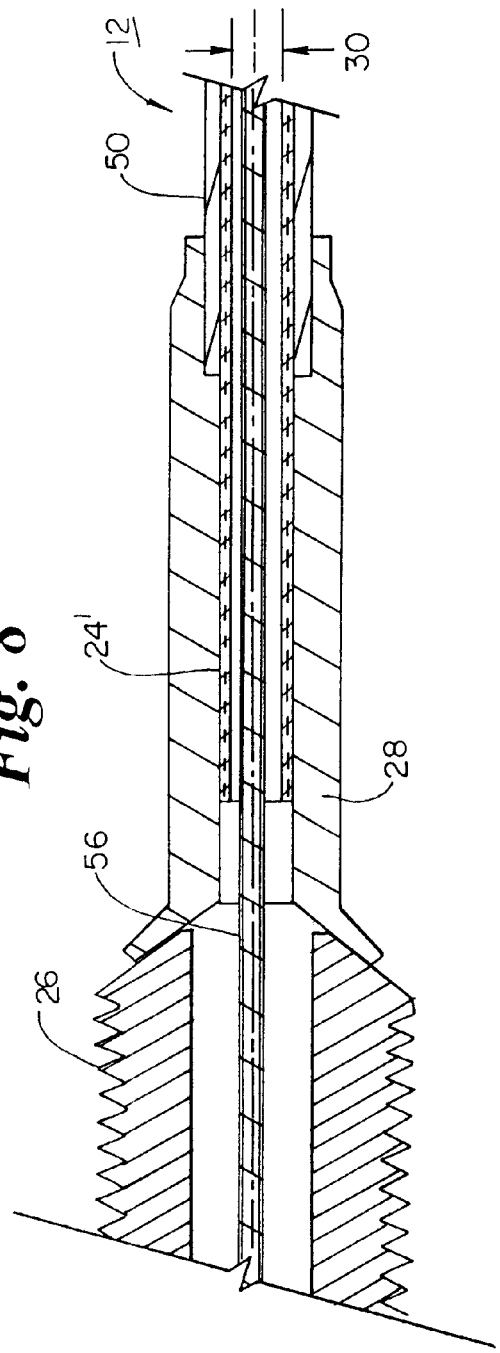

INFUSION WIRE HAVING FIXED CORE WIRE

This application is a continuation-in-part of pending U.S. patent application Ser. No. 08/541,147 filed Oct. 11, 1995.

BACKGROUND OF THE INVENTION

1. Field of the Invention

The present invention relates to medical catheters and guidewires commonly used in the placement of catheters in a patient's vascular system, and particularly to infusion wires that can be used both as a guidewire or an infusion catheter.

2. Description of the Background Art

Medical catheters and guidewires are devices that can be navigated through narrow body passages, typically blood vessels, until the distal end section is in a desired location. Guidewires are typically used for introduction of a catheter over the guidewire in order to perform a medical procedure in a blood vessel or body organ. For example, guidewires are employed to traverse blood vessels to reach a desired site. Then a catheter is advanced over the guidewire to a desired orientation with respect to the site for delivery of a drug or agent or for a performing a therapeutic or diagnostic function.

Cardiovascular guidewires typically have a solid core wire and are dimensioned to be received within a catheter lumen as the catheter is advanced over the guidewire. One very common guidewire construction has an elongated, flexible, helical coil having a proximal end and a distal end, the latter being inserted into the patient's vascular system. The internal core wire typically extends through the coil lumen with the proximal and distal ends of the core wire attached to the proximal and distal ends of the coil. A physician controls the advancement and resulting position of the distal end of the guidewire by manipulations performed at the proximal end outside the body. Then, a catheter is advanced over the guidewire, which may be left in place or withdrawn during a procedure using the guidewire.

In order to advance the catheter over the guidewire, it must be uniform in outer diameter or have only step down diameter reductions and minimal diameter increases distally. In addition, both catheters and guidewires are preferably constructed with radiopaque markers that are have greater radiopacity and hence higher visibility under fluoroscopy than the bulk of the elongated catheter or guidewire body. These markers allow the physician to visualize the location of the distal end and/or intermediate point(s) along the elongated body within the patient's body. When both the guidewire and the catheter are provided with such markers, care must be taken that they are not so long on one or both device that they mask one another or are confusing. In this regard, it may not be desirable to make the entire wire coil in the distal segment or portion of a high density radiopaque material, because its bright appearance under fluoroscopy would mask any radiopaque marker(s) on the catheter being introduced over it.

Some guidewires are constructed of wire coil defining a guidewire lumen with an outer sheath surrounding or within the wire coil and are adapted for use both as guidewires and as infusion catheters and are referred to as infusion wires. An infusion wire having a number of advantages is disclosed in commonly assigned U.S. Pat. No. 5,554,114. The infusion wire body disclosed in the '114 patent employs a wire coil extending within or outside a sheath for containing the infused drug or agent. Further wire coil infusion wires are disclosed, for example, in U.S. Pat. Nos. 5,178,158, 5,184, 627, and 5,211,636. These infusion wires are provided with either a distal axial open end hole or a closed distal end with infusion side holes and a lumen for conveying infusion fluids or body fluids between the proximal end and the end hole or side holes.

In order to operate as a guide wire and be advanced through a tortuous vascular pathway to a desired infusion site, it is necessary that the overall outer diameter be as small as possible and that the construction provide for ease of advancement and excellent steerability or torqueability from the manipulated proximal end to the distal end thereof. Moreover, the construction typically requires increasing flexibility in the intermediate and distal sections. In order to provide adequate infusion capabilities, the side wall thickness has to be minimized to maximize potential infusion volume. The side wall construction also has to withstand high fluid pressures during infusion.

In use, because of the narrow gauge, flexibility and column strength, the distal portion of an infusion wire can be advanced to a desired site in a blood vessel. Then, the physician can advance a catheter over the infusion wire to the site. Depending on the design, the physician can remove the infusion wire from the catheter lumen or leave it in place while conducting a procedure with the catheter. Drugs or agents can be infused from the proximal end of the infusion wire, through the infusion lumen, and out through the distal end lumen opening or through a plurality of side holes in the distal sheath and/or through spaces between exposed turns of distal wire coil, if any, during or following the procedure using the catheter. Alternatively, distal blood pressure may be monitored through a fluid column in the lumen. Typical uses of infusion wires to infuse thrombolytic agents into a thrombus in a blood vessel to dissolve it are described in the article by T. McNamara, M.D. et al. entitled "Coaxial system improves thrombolysis of ischemia" published in DIAGNOSTIC IMAGING (pp. 122–131, November 1991), and incorporated herein by reference in its entirety.

A particular infusion wire is disclosed in U.S. Pat. No. 5,322,508 wherein a partial length core wire is attached at the distal end of a metal hypotube infusion wire body and extends distally within a wire coil also attached at the distal end of the hypotube. Hypotube construction without a full length core wire may provide a maximal size cross-section, infusion lumen that may accommodate a relatively high infusion flow rate. However, the constriction at the attachment to the distal core wire extension before the distal infusion side holes negates the advantage imparted by the unobstructed hypotube lumen. Moreover, hypotube does not provide for a 1:1 torque transmission down the length of the infusion wire during twisting or rotational advancement.

A further U.S. Pat. No. 5,569,197 discloses a similar infusion wire to those disclosed in the above-referenced patents and McNamara article that uses a superelastic alloy as a particular hypotube material in the proximal portion of the infusion wire. A number of conventional uses of infusion wires, e.g., to guide balloon angioplasty and stent placement balloon catheters into a desired site, are also disclosed in the '197 patent.

Currently, there are two types of clinically used infusion wires, one having a closed end of the type disclosed in the '627 patent and another having an open end of the type disclosed in the '158 patent and sometimes referred to as a "convertible wire". The '158 and '627 patents describe infusion wires and convertible wires having full length, coiled wire bodies within outer sheaths with constant diameter infusion lumens. In each case, the proximal sections have a polyimide tube between the wire coil and the outer sheath to strengthen that section and allow increased infusate pressure. The convertible wire disclosed in the '158 patent delivers the infusate through a distal end hole of the infusion lumen. The infusion wire disclosed in the '627 patent has a closed distal end and a plurality of infusion side holes cut in the outer sheath which covers the wire coil. In both cases, the removable core wire supplies sufficient column strength for steerability as the convertible wire or infusion wire is advanced to the treatment site.

In use of these infusion wires and convertible wires, when infusion therapy is desired, the core wire must be completely removed, since it occupies the bulk of the infusion lumen and would increase flow resistance and decrease flow rate dramatically were it left in place. The handling of this core wire is bothersome to many physicians. In addition, because of the full length coil construction (and non-attached core wire), it has no steerability or torqueability. Physicians may desire to steer the distal end into another vessel after the infusion wire is already deployed. Without the ability to steer the tip, they often will be forced to withdraw the entire convertible wire, then place a regular guidewire at the desired site, follow it with an infusion catheter advanced over the guidewire, and then remove the regular guidewire and replace it with the infusion wire.

While the '636 patent discloses an integral core wire within the infusion lumen of an infusion wire, the depicted embodiments all have at least one full length outer wire coil and a coaxial sheath leaving a small cross-section area for the infusion of infusate at slow, steady rates. A high pressure drop is effected along the length of the infusion wire so that the slow infusion rate between the distal coil wire turns and the infusion pressure is relatively insensitive to the fluid pressure of the fluid entering the lumen at the proximal end.

Infusion wires require a small cross-section size (typically 0.038 inches or less in diameter) and preferably have a relatively stiff proximal infusion wire portion to transmit torque and allow the infusion wire to be pushed and steered through the vascular system to position the distal infusion wire portion at a desired site. Such infusion wires also preferably have a relatively flexible distal infusion wire portion in order to access small diameter and tortuous body vessels. The stiffness and flexibility are controlled by the construction employing a removable or permanent core wire, the coiled wire in at least the distal infusion wire portion and a variety of proximal portion side wall constructions as described above.

Infusion wires also require at least one impervious sheath extending from the proximal end to one or more infusion port at or near the distal end in order to contain the infusate fluid. The delivery of infusate along the distal portion of the infusion wires of these types is effected typically through infusate passageways including the infusion lumen space extending along the length of the infusion wire between the core wire and the coiled wire within the impervious sheath, referred to as the infusion lumen, and then through the spaces between the adjacent wire coil turns and through one or more side opening in the sheath in the distal portion. The cross-section area of the passageways affects the volume of infusate that can be delivered through the proximal and distal infusion wire portions. The conflicting demands for passageway cross-section area and sufficient stiffness and flexibility in the infusion wire portions are difficult to satisfy.

In order to deliver the infusate along the distal portion, the sheath may terminate proximally to the infusion wire distal end, leaving a side opening comprising number of exposed distal coil wire turns, as in the above-referenced '508 patent. Alternatively, one or more typically a plurality of slits or holes are formed through the impervious sheath, as in the above-referenced '627 patent through which the infusate is expelled laterally. In either case, the infusate may be unevenly expelled first through the spacings between wire coil turns and then through the sheath opening or openings.

It is also desirable to be able to manually shape at least the distal most section of the distal infusion wire portion into a curve for accessing blood vessels during introduction of the infusion wire. At times, the applied force can cause the distal infusion wire portion to kink.

An infusion wire with improved steerability, uniformity in infusate fluid delivery profile, enhanced capability to be shaped to ease introduction into difficult to access blood vessels, and retaining a high infusion flow rate would therefore be a great improvement.

SUMMARY OF THE INVENTION

It is therefore a principal object of the present invention to provide an infusion wire of minimal outer diameter having an improved torqueability and steerability while maximizing the unobstructed diameter of the infusion lumen and the flow rate of infusate.

It is a further object of the present invention to provide an improved infusion wire having an improved infusate delivery profile along the infusion length thereof.

It is a still further object of the invention to provide such an infusion wire having improved resistance to kinking in the distal infusion wire portion.

These and other objects of the invention are realized in a flexible elongated medical infusion wire having proximal and distal infusion wire portions between infusion wire proximal and distal ends adapted for introduction through a selected path in a patient's body to a site in a blood vessel or body cavity and for infusing an infusate fluid drug or agent into the blood vessel or body cavity. A flexible, elongated tubular, inner sheath having an inner sheath lumen formed therein extends from the infusion wire proximal end and distally through the proximal infusion wire portion to an intermediate junction. A flexible, elongated, helically wound, distal wire coil having a distal coil lumen formed therein extends from the infusion wire distal end and proximally through the distal infusion wire portion to the junction with the distal end of the inner sheath. An elongated, tubular outer sheath extends between the proximal and distal infusion wire ends having an outer sheath lumen formed therein for receiving the inner sheath in a proximal sheath portion thereof and for receiving the distal wire coil in a distal sheath portion thereof. The inner sheath lumen and the distal coil lumen are substantially aligned to a common axis at the intermediate junction. The outer sheath is formed with a plurality of infusion ports formed therein in the distal sheath portion thereof for allowing transmission of infusate fluids between the infusion lumen, adjacent turns of the distal wire coil and the infusion port to the exterior of the distal sheath portion.

An elongated stiffening core wire having a proximal core wire end and a distal core wire end is positioned within the aligned inner sheath lumen and wire coil lumen to extend therein from the proximal infusion wire end to the distal infusion wire end. An infusion lumen is defined by the cross-section area within the aligned inner sheath lumen and wire coil lumen that is not occupied by the elongated stiffening core wire.

In one feature of the present invention, the flexible, elongated tubular, inner sheath is formed of wire reinforced, polyimide providing resistance to collapse of the inner sheath and enhanced torque transmission through the proximal infusion wire portion in use of the infusion wire.

In another feature of the invention, the distal wire coil has a proximal wire coil section and a distal wire coil section, the proximal wire coil section close wound at a close coil pitch and the distal wire coil section space wound at a space wound coil pitch to accomplish a predetermined flow rate of fluids flowing between the space wound wire turns of the space wound distal wire coil section. Preferably the space between adjacent wire turns increases distally in the distal wire coil section.

In a further feature of the present invention, the core wire comprises a proximal core wire portion and a distal core wire portion. The proximal core wire portion is formed with a proximal core wire portion diameter smaller than the infusion diameter in the proximal infusion wire portion. The distal core wire portion is formed of a proximal core wire section and a distal core wire section. The proximal core wire section is formed with a proximal core wire section diameter smaller than the proximal core wire portion diameter, and the distal core wire section is formed with a distal core wire section diameter smaller than the proximal core wire section diameter. A tapered proximal transition zone extends between the proximal core wire portion and the proximal core wire section, and a tapered distal transition zone extends between the proximal and distal core wire sections.

The infusion wire of the present invention provides enhanced handling advantages and infusate flow rates equal to or exceeding conventional infusion wires or convertible wires, while retaining the core wire in place. This allows the physician to avoid removing and replacing the infusion wire with a regular guidewire as described above.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 1 is a plan view of an infusion wire according to the various embodiments of the present invention;

FIG. 2 is an end view (cross section) of the infusion wire proximal end assembly of the infusion wire of FIG. 1;

FIG. 3 is a side cross-section view of the infusion wire proximal end assembly of the infusion wire of FIG. 1;

FIG. 4 is a partial cross-section plan view of the infusion wire in accordance with the first embodiment of the invention depicting the transition between the proximal and distal infusion wire portions thereof;

FIG. 5 is a partial cross-section plan view of the distal section of the infusion wire distal portion in accordance with the first embodiment of the invention;

FIG. 6 is a partial cross-section plan view of a variation of the infusion wire of FIG. 4 including an integral radiopaque marker in accordance with a further aspect of the invention;

FIG. 7 is a plan view of an infusion wire according to the second preferred embodiment of the present invention;

FIG. 8 is an expanded partial side cross-section view of the infusion wire proximal end assembly of the infusion wire of FIG. 7;

DETAILED DESCRIPTION OF THE PREFERRED EMBODIMENTS

Figure 10:
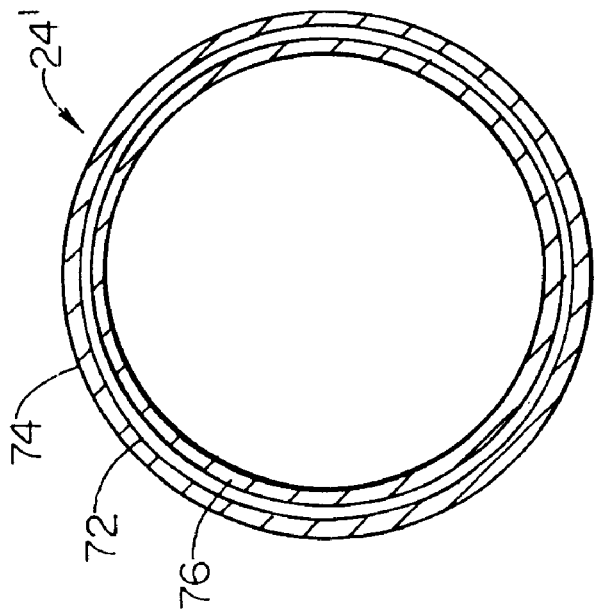
FIG. 10 is an expanded, end view of the inner sheath of FIG. 9.

Turning now to FIGS. 1–3, they generally depict the construction of an infusion wire 10 in accordance with the preferred embodiments of the present invention. FIGS. 4–6 depict the construction of the distal portion of the infusion wire in accordance with a first preferred embodiment of the invention. FIGS. 7–12 depict the construction of features of the infusion wire of the second preferred embodiment of the invention. It will be understood that further preferred embodiments are generally disclosed wherein certain of the features of the second preferred embodiment are separately employed in an infusion wire conforming with the first embodiment of the invention.

The flexible, elongated, medical infusion wire 10 of the embodiments of the present invention has a proximal infusion wire portion 12 and distal infusion wire portion 14 joined together at a junction 36 and extending between infusion wire proximal end 16 and infusion wire distal end 18. The infusion wire 10 is adapted for introduction through a selected path in a patient's body to a site in a blood vessel or body cavity and for infusing an infusate fluid drug or agent into the blood vessel or body cavity. Preferably, the overall usable length of the infusion wire 10 is on the order of 145 cm to 175 cm, for example. The infusion wire 10 preferably has a maximum outer diameter of about 0.035 inches. The distal infusion wire portion 14 preferably ranges from about 3.0 cm to about 20.0 cm in length.

As shown in FIGS. 1–3, the proximal infusion wire portion 12 includes the luer connector housing 20 and the flexible, elongated, tubular, inner sheath 24 of a first length extending from the infusion wire proximal end 16 and distally through the proximal infusion wire portion 12 having an inner sheath lumen 30 formed thereby. The inner sheath 24 is preferably composed of a high strength, thin walled, flexible tubing. The proximal end of the inner sheath 24 is sealed within the lumen at one end of a strain relief 28 which is flared and compression fit at its other end between the male connector fitting 26 and a threaded female connector nut 32 threaded over it. In the first embodiment, the inner sheath 24 is preferably formed of a solid polyimide tube that is 0.0295 inches in outer diameter and 0.0275 inches inner diameter, for example, that defines an inner sheath lumen 30 therein. In the second embodiment shown in FIGS. 7–12, the inner sheath is preferably formed of a wire reinforced polyimide tube in at least a proximal inner sheath section thereof that retains flexibility while reinforcing the proximal infusion wire portion 12 to resist collapse of the inner sheath 24 and to provide enhanced torque transmission and pushability in use of the infusion wire 10.

As shown in FIGS. 4 and 6, the inner sheath 24 extends distally through the proximal portion 12 to an intermediate junction 36 where it terminates. The proximal end of a flexible, elongated, helically wound, distal, wire coil 40 extending to a distal wire coil end thereof at the infusion wire distal end 18 is forced into the distal end of an inner sheath lumen 30 of the polyimide sheath 24 along the short overlapping lengths thereof at the intermediate junction 36. The wire coil 40 preferably is formed of circular cross-section stainless steel wire of about 0.004 inches diameter wound into a wire coil having an inner diameter of about 0.021 inches defining a wire coil infusion lumen 42 and an outer diameter of about 0.029 inches.

Returning to FIG. 1, an elongated, flexible, tubular, outer sheath 50 extends through the proximal and distal infusion wire portions 12 and 14. The outer sheath 50 has an outer sheath lumen 52 formed therein for receiving the inner sheath 24 in a proximal portion thereof and the distal wire coil 40 in a distal portion thereof The inner sheath lumen 30 and the distal wire coil lumen 42 are substantially co-axially aligned at their junction 36 and define an infusion lumen 34 having an infusion diameter that is stepped down slightly through and distally to junction 36. The outer sheath 50 provides a substantially constant outer diameter through the length of the infusion wire 10. The outer sheath 50 has at least one infusion port 54, formed therein in the distal portion thereof for allowing transmission of fluids between the infusion lumen, adjacent enclosed turns of the distal wire coil 40 and the infusion port(s) 54, to the exterior of the distal portion of the outer sheath 50. Preferably, the number n and the spacings apart of the infusion ports $54_n$ may be selected as a function of the length of distal portion 14. For example, the number n=8for3.0 cm length, n=14 for 6.0 cm, n=20 for9.0 cm, and n=26 for 12.0cm.

The outer sheath 50 is preferably a Teflon® (PTFE) shrink tube that is optically substantially transparent and that can be heat shrunk over the entire assembly of the inner polyimide sheath 24 and the distal wire coil 40 to lock the assembly in place and provide a lubricious outer surface. Prior to applying heat, the side holes or infusion ports $54_n$ are cut in or formed in the distal portion of the tube that will be shrunk over the separated turns of distal wire coil 40. At the intermediate junction 36, the shrunken outer sheath 50 locks the assembly together without the need for adhesives, braze, solder or the like, retaining flexibility along the length of junction 36.

An elongated, stiffening, core wire 56 extends from the infusion wire proximal end 16 to the infusion wire distal end 18. The proximal end of the core wire 56 is attached to the proximal luer connector housing 20 and thereby to the proximal ends of the tubular inner and outer sheaths 24 and 50. The distal end of the core wire 56 is attached to the infusion wire distal end as shown in FIG. 5 of the first embodiment and FIG. 11 of the second embodiment and described below. The core wire 56 is otherwise not attached within the infusion lumen to components of the infusion wire 10. The attachment of the core wire at the infusion wire proximal and distal ends 16 and 18 enables steering of the infusion wire distal end 18 by manually rotating the connector housing 20.

As shown in FIG. 3, the proximal core wire end 58 is bent into a shape which fits into a keyed groove 38 inside the connector housing 20. The connector housing 20 includes a hub member 62 having an outer surface 64 adapted to be manually engaged and manipulated to advance and rotate infusion wire 10 through a blood vessel. The hub member 62 has an internal conduit 66 therein for transmission of infusion fluids to the infusion lumen 34 and for receiving the proximal core wire end 58. The proximal core wire end 58 is formed with a laterally bent shape in one plane of a size to prevent the bent shape from being advanced distally through the conduit 66 and the aligned infusion lumen 34 and for fixing the core wire 56 from rotation in the conduit 66 and the infusion lumen 34 during advancement and rotation of the infusion wire 10. A pair of planar side walls 68, 70 extend laterally on either side from the conduit 66 within the hub member 62 to form the cavity of the keyed groove 38 for receiving the bent shape of the proximal core wire end 58 and for restraining rotation thereof. The bent shape, proximal core wire end 58 can alternatively be insert molded into the proximal connector housing 20, leaving the conduit 66 open.

Specific features of the first embodiment of the invention are depicted in the fabrication and assembly of the core wire 56 and distal wire coil 40 in the distal infusion wire portion 14 depicted in FIGS. 4–6. The elongated stiffening core wire 56 extends from the proximal core wire end 58 shown in FIGS. 2 and 3 to a distal core wire end 60. The stiffening core wire 56 is positioned within the aligned axial inner sheath and wire coil lumens 30 and 42, to extend between the proximal and distal infusion wire ends 16 and 18, thereby defining the infusion lumen 34 in the space not occupied by the core wire 56. In a preferred example, the integral stiffening core wire 56 consists of a 0.010–0.016 inch diameter, stainless steel core wire which tapers to 0.0030–0.0065 inches at the distal end 18. A continuous taper is commenced just proximal to the junction of inner polyimide sheath 24 and distal wire coil 40. Ideally, a 0.009" diameter portion of the taper is located at the most proximal end of the distal wire coil 40. The tapering provides a relatively constant cross-section area infusate passageway within the infusion lumen not occupied by the core wire 56, despite narrowing of the infusion lumen 34 at and distally to the junction 36.

The integral core wire 56 is brazed, for example, at its distal core wire end 60 to the distal end turns of the distal wire coil 40 forming an attachment ball 44 as shown in FIG. 5. The brazing creates the integral attachment of the core wire end 60 that provides for increased steerability and torque transfer. The core wire distal end 60 may be flattened prior to brazing in order to create a mechanical lock for a stronger braze pull force. The distal core wire end 60 and distal wire coil 40 can also be soldered or welded or attached with adhesive, but brazing is preferred. A platinum marker tube 46 made from a short length of platinum tubing is encapsulated in the attachment ball 44 (or other attachment means) between the core wire 56 and the distal wire coil 40. The attachment ball 44 also serves to close the distal end of the infusion wire to internal infusate pressure. This is effected when the outer sheath 50 is heat shrunk. The tip of the heat shrink tube sheath 50 is shrunk past the attachment ball 44 to lock it in, and any remaining distal tail is trimmed short to about 0.015 inches in length.

In use, rotational motion imparted to the hub member outer surface 64 is imparted to the core wire 56 and through the core wire 56 to the attachment ball 44 attaching the distal core wire end 60 to the distal end of the distal wire coil 40 within the outer sheath 50. Because the distal end of the core wire 56 is brazed to the distal end of distal wire coil 40, the infusion wire distal end 18 will be steerable. The core wire 56 can be shaped at the infusion wire distal end 18 by the physician to improve the steerability.

In order to allow the passage of infusate between the inner infusion lumen and the infusion port(s), the adjacent turns of the distal wire coil 40 shown in FIGS. 4–6 are separated by approximately one-half the wire diameter or about 0.002 inches. The tapered core wire 56 within the aligned inner sheath lumen 30 and distal wire coil lumen 42 and the integral attachment of proximal and distal core wire ends 58, 60 as described above replaces the full length wire coils of the side hole infusing infusion wires of the above-referenced '627, and '636 patents. The resulting net cross-section area provides an infusion lumen 34 within the same outer diameter that allows a flow rate exceeding or comparable to the flow rates of the side hole infusing infusion wires of the '636 and '627 patents, respectively. For example, the infusion flow rates for room temperature water at 100 psi are specified for the following differing infusion lengths:

| | |
|---|---|
| 3.0 cm | 28 cc/min |
| 6.0 cm | 30 cc/min |
| 9.0 cm | 32 cc/min |
| 12.0 cm | 34 cc/min |

In use of the infusion wire 10, both slow drip, i.e., weeping, infusion and spray infusion may be effected. The infusion wire 10 is further specified to withstand pressures of up to 350 psi without bursting or tip leakage.

Turning to a further aspect of the present invention, as shown in FIG. 6, platinum spring marker wire coil 48, preferably made in the same 0.004 inch wire diameter and coiled with the same pitch, inside diameter and outside diameter as the wire coil 40, is screwed into the turns of the distal wire coil 40. The wire coils 40 and 48 are both wound in the same direction preferably with a gap of one-quarter to one times wire diameter. This allows the two coils to be screwed together preferably over a close fitting mandrel. The platinum marker wire coil 48 can be short (e.g. 0.050" long), and the coil turns need only to be wound together a few times to provide a good lock.

The two wire coils 48 and 40 are screwed together to form a high radiopacity marker of about 0.075 inches long. Both ends of the platinum marker wire coil 48 and a number of turns of the proximal end of the stainless steel distal wire coil 40 are forced into an interference fit within the distal end opening of inner sheath lumen 30. The inner sheath lumen 30 protects and holds the ends of the wire coil 48 turns from moving laterally, and maintains the diameter of the distal wire coil lumen 42 constant, and the outer sheath 50 prevents longitudinal displacement or separation of the intertwined coil turns from the inner sheath lumen 30 without requiring an adhesive, braze or solder. The platinum wire coil 48 turns at the proximal end of the stainless distal wire coil 40 thereby serve as a radiopaque marker to mark the proximal end of the infusion section.

Because the platinum wire coil is wound in an intertwined manner with the stainless wire coil, there is no reduction of a lumen diameter or increase in the outer diameter at the marker section. The resulting joint provides a radiopaque marker that can be readily seen under fluoroscopy, yet which maintains the identical inner and outer diameter as a less radiopaque stainless steel coil and virtually the same flexibility without a marker. The resulting product has an outer surface with no bumps or increases in diameter and an inner lumen with no added restrictions to flow or to tracking over a guide wire.

Figure 11:
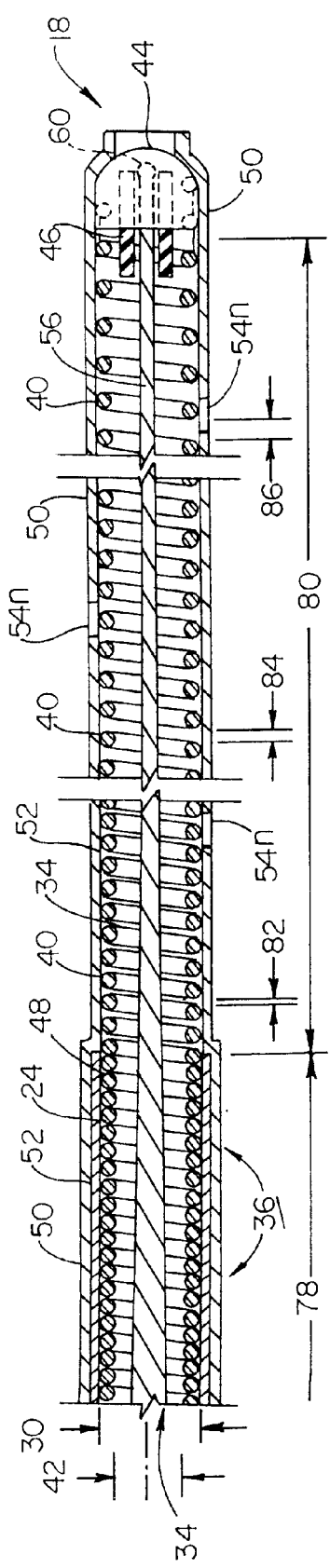
FIG. 11 is a side cross-section view of the distal infusion wire portion of the infusion wire of FIG. 7 depicting the preferred coil spacings between adjacent wire coil turns of the wire coil.

FIGS. 7–12 depict three features of the second embodiment of the invention which are preferably practiced in conjunction with one another in an improved infusion wire 10'. However, it is contemplated that one or two of the features may be substituted for like features of the first embodiment. These features include a strengthened inner sheath 24' (shown in FIGS. 7–10) in at least a proximal section thereof to make the proximal infusion wire portion 12 more resistant to collapse from pressure applied around its perimeter to seal it within a fitting. In addition, the reinforcement of the strengthened inner sheath 24' makes it easier to transmit torque manually applied at the luer connector housing 20 through the proximal infusion wire portion 12 to the distal infusion wire portion 14. The second feature comprises varying the pitch of the distal wire coil through at least a distal section of the length of the distal infusion wire portion 14 to distribute infusate more evenly to the plurality of longitudinally spaced apart infusion ports $54_n$ as shown in FIG. 11. The third feature comprises changing the shape of the stiffening core wire 56 in the distal infusion wire portion 14 from the single continuous taper of the first embodiment to a stepped double taper to increase the flexibility of a distal section thereof to increase the cross-section infusion area of the infusion lumen 34 distally, and to improve resistance to kinking of the core wire 56 just distally of the intermediate junction 36.

FIGS. 7–10 depict the improved, flexible, elongated, tubular, inner sheath 24' formed of wire reinforced, polyimide within at least a proximal inner sheath section 106 to provide greater compression strength and enhanced torque transmission through the proximal infusion wire portion 12 in use of the infusion wire 10. As in the first embodiment, the improved inner sheath 24' has an inner sheath lumen 30 formed therein and extends from the infusion wire proximal end 16 and distally through the proximal infusion wire portion 12 to the intermediate junction 36. The reinforcement of the improved inner sheath 24' is effected by a flattened, space wound, coiled wire 72 embedded between a nominally designated inner sheath outer layer 74 and an inner sheath inner layer 76, both formed of polyimide in at least the inner sheath section 106. The space wound, coiled wire 72 increases the crush resistance of the polyimide tube in the proximal inner sheath section 106. Preferably the distal inner sheath section 108 is devoid of the coiled wire 72 in order to maintain the flexibility of the proximal infusion wire portion 12.

Figure 9:
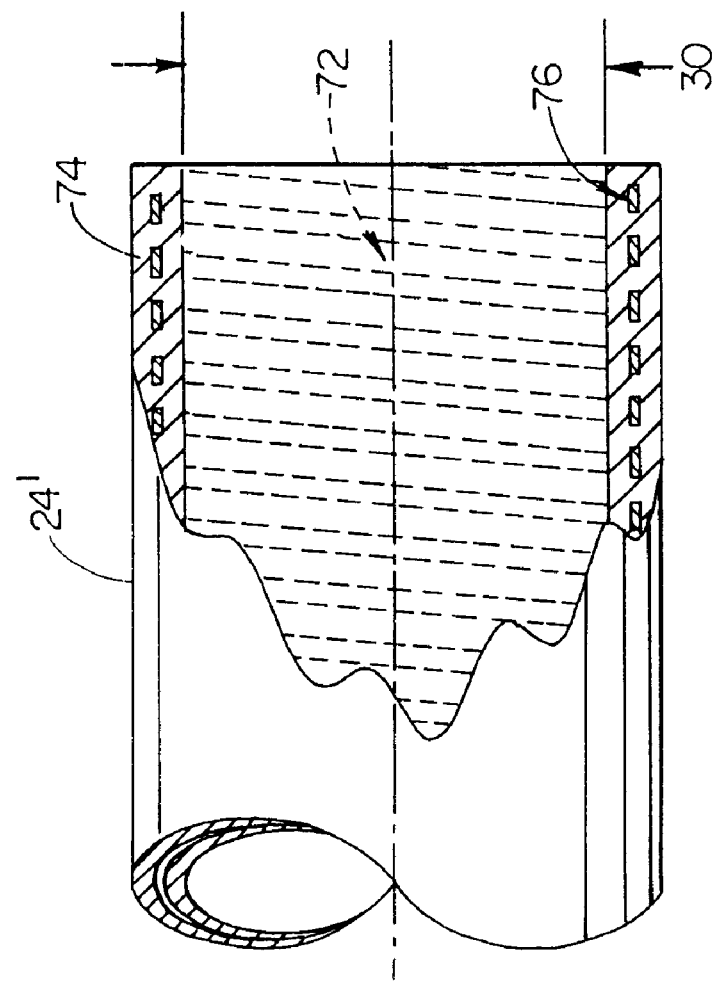
FIG. 9 is an expanded, partial side cross-section view of a proximal inner sheath section situated within at least a proximal section of the proximal infusion wire portion of the infusion wire of FIG. 7.

Preferably, the coiled wire 72 is formed of stainless steel, and the process of embedding the coiled wire 72 may be effected by coating or extrusion such that the nominally designated, inner sheath, outer and inner layers 74 and 76 are in fact a single layer of polyimide. It will also be realized to those of skill in the art that the smooth wall surfaces of the inner sheath, outer and inner layers 74 and 76 shown in FIGS. 8–10 are an idealized representation. In practice, the surfaces are corrugated in a spiral pattern tracking the turns of the embedded coiled wire 72 as shown in FIG. 7. The corrugated spiral pattern of the exterior surface of the inner sheath outer layer 74 can be seen as illustrated in FIG. 7 and felt tactually through the thin, transparent, outer sheath 50 after it is shrunk fit over the improved inner sheath 24'.

In a typical therapeutic procedure, the infusion wire 10' is used coaxially with a balloon catheter or an infusion catheter in the manner described in the above-incorporated McNamara article. As described therein, in one procedure, the inner infusion wire 10' is introduced through the O-ring seal of a Touhy-Borst type adaptor attached to the hub of the outer catheter until the distal infusion wire portion 14 exits through the distal end opening of the infusion catheter to position the infusion exit ports $54_n$ in relation to a thrombus to be dissolved by the infused thrombolytic agent. Alternatively, the outer catheter may be introduced over a previously introduced and positioned infusion wire. In either case, the seal of the O-ring against the exterior surface of the proximal infusion wire portion 12 may be tightened to avoid leakage and create a risk of collapsing it and squeezing off the infusion lumen 34. The reinforcement of the improved inner sheath 24' in at least the proximal inner sheath section 106 diminishes that risk while retaining flexibility through the remainder of the proximal infusion wire portion 12. In addition, it enhances the column strength and torque transmission capability so that the proximal and distal infusion wire portions 12 and 14 can be rotated and steered through tortuous blood vessels.

It is contemplated that the infusion wire of the second preferred embodiment will be supplied in one or more overall length from 145 cm–175 cm, for example, and with designated infusion lengths of the distal infusion wire portion 14, e.g., 3.0 cm, 6.0 cm, 9.0 cm and 12.0 cm, for example. It is also contemplated that the length of the proximal inner sheath section 106 will be fixed at about 82.5 cm, for example, regardless of the overall length or the infusion segment length. Consequently, the length of the distal inner sheath section 108 will vary depending on the overall length of the infusion wire 10' and the distal infusion wire portion 14.

Turning to FIG. 11, it depicts the distal end portion of the infusion wire 10' wherein the distal core wire end 60 is preferably welded to the distal end turns of the wire coil 40 and the platinum marker tube 46 forming attachment ball 44. FIG. 11 also shows varying the pitch of the distal wire coil through at least a distal section of the length of the distal infusion wire portion 14 to distribute infusate more evenly to the plurality of longitudinally spaced apart infusion ports $54_n$. The plurality "n" of infusion ports $54_n$ are distributed in a pattern, e.g. one or more spiral pattern extending around the circumference of the outer sheath 50. The infusion ports $54_n$ are distributed over an infusion length extending along a distal section of the distal infusion wire portion between the junction 36 and the welded attachment ball 44. Assuming that the infusion ports $54_n$ are equally sized, the infusate delivered under pressure through the infusion lumen 34 has the tendency to exit in greatest volume through the most proximal infusion ports $54_n$, so that the volume of infusate fluids delivered along the infusion length diminishes distally. Moreover, the pressure of the infusate within the infusion lumen 34 decreases distally as the infusate fluid escapes through the more proximal infusion ports $54_n$.

As described above, the flexible, elongated, helically wound, wire coil 40 has a distal coil lumen 42 formed therein extending distally from the intermediate junction 36 through the distal infusion wire portion 14 to the infusion wire distal end 18 where it is obstructed by the attachment ball 44. The wire coil 40 has a proximal wire coil section 78 and a distal wire coil section 80. The proximal wire coil section 78 is close wound at a close coil winding pitch so that the most proximal adjacent turns contact one another. In this particular illustrated embodiment, the above-described radiopaque, platinum marker wire coil 48 is also intertwined between turns of the wire coil 40 in the proximal wire coil section 78 in a close wound manner. The proximal wire coil section 78 and the intertwined marker wire coil 48 are received within the distal end opening of the distal inner sheath section 108 at the junction 36.

In accordance with this aspect of the present invention, coil wire turns in the distal wire coil section 80 are space wound at a space wound coil pitch that increases the spacing between adjacent coil turns distally. This distally increasing spacing is provided so that the volume of infusate delivered between the coil turns can increase distally to distally bias the flow of infusate between the spaced turns and equalize infusate pressure along the infusion lumen 34 and infusate volume delivered through the infusion ports $54_n$. To this end, the proximal coil wire turns in the distal wire coil section 80 are initially spaced apart by a narrow coil spacing 82 which may be on the order of about 0.0005 inches to 0.0008 inches, for example. The coil spacing is increased distally to an intermediate coil spacing 84, which may be on the order of 0.0010 inches, for example, and to a distal coil spacing 86, which may be on the order of about 0.0015 inches or greater, for example, depending on the overall length of the distal wire coil section 80. The coil spacing increase distally may be continuous or stepped and tailored to accomplish a predetermined flow rate of infusate fluids flowing through the spacings between the space wound coil turns and then from the plurality of infusion ports $54_n$.

Figure 12:
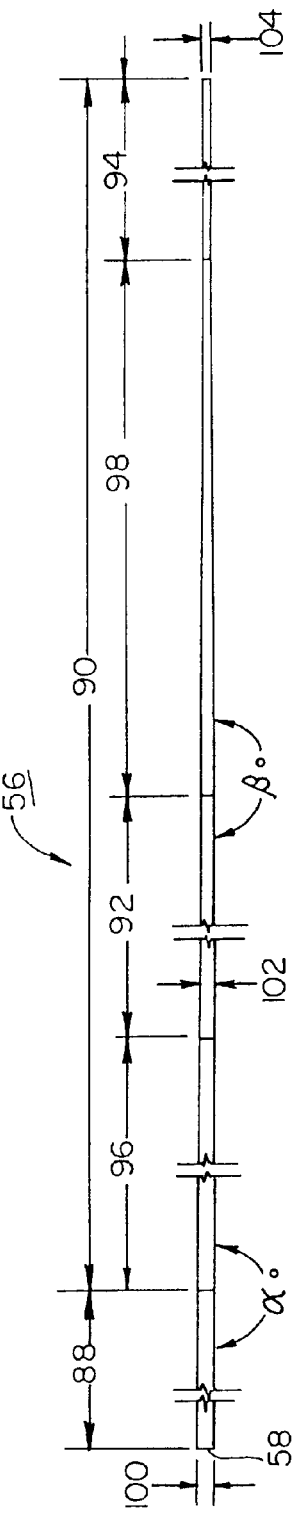
FIG. 12 is a side view of a fixed core wire inserted into the infusion wire lumen and preferably employed in the second embodiment of the invention.

The third feature comprising changing the shape of the stiffening core wire 56 in the distal infusion wire portion 14 from the single continuous taper of the first embodiment to a stepped double taper to increase the flexibility of a distal section thereof, to increase the cross-section infusion area of the infusion lumen 34 distally, and to improve resistance to kinking of the core wire 56 just distally of the intermediate junction 36 is shown in FIG. 12. The elongated stiffening core wire 56 having a proximal core wire end 58 and a distal core wire end 60 is positioned within the infusion lumen 34 to extend therein from the proximal infusion wire end 16 to the distal infusion wire end 18 as shown in FIGS. 1–3 and 11. The core wire 56 comprises a proximal core wire portion 88 and a distal core wire portion 90 extending in an overall length of about 60.0 inches or 81.0 inches, depending on the overall length of the infusion wire 10. The proximal core wire portion 88 extends the length of the proximal infusion wire portion 12.

The proximal core wire portion 88 is formed with a proximal core wire portion diameter 100 smaller than the diameter of the inner sheath lumen 30. The proximal core wire portion diameter 100 at the junction with the distal core wire portion 90 is preferably on the order of about 0.0130 inches, for example. The distal core wire portion 90 is further formed of a proximal core wire section 92 of about 3.50 inches in length, for example, and a distal core wire section 94 of about 2.50 inches in length, for example. The proximal core wire section 92 is formed with a constant proximal core wire section diameter 102 that is smaller than the proximal core wire portion 88, preferably on the order of about 0.0090 inches, for example. The distal core wire section 94 is preferably formed with a constant distal core wire section diameter 104 that is smaller than the proximal core wire section diameter 102, preferably on the order of about 0.0055 inches for example.

A proximal core wire transition zone 96 extends between the proximal core wire portion 88 and the proximal core wire section 92 of the distal core wire portion 90 for a length of about 1.9 inches, for example. The proximal core wire transition zone is 96 tapered to provide a reduction in diameter of the core wire 56 from the proximal core wire portion diameter 100 to the proximal core wire section diameter 102. Similarly, a distal core wire transition zone 98 extends between the proximal core wire section 92 and the distal core wire section 94 for a length of about 0.41 inches, for example. The distal core wire transition zone 98 is tapered to provide a reduction in diameter of the core wire 56 from the proximal core wire section diameter 102 to the distal core wire section diameter 104.

In this manner, the cross-section area of the infusion lumen 34 increases distally through the distal infusion wire portion 14 in a step-wise manner, as opposed to the continuous manner in the first embodiment. The proximal core wire transition zone 96 and the proximal core wire section 92 are positioned to bridge the intermediate junction 36 and provide an increasing flexibility distally that lessens the tendency of the distal infusion wire portion to kink when bent distally of the intermediate junction 36. The distal core wire transition zone 98 and the reduced diameter distal core wire section 94 allow them to be manually curved to form a bend in the most distal section of the distal infusion wire portion 14 to aid in steering it through tortuous blood vessels. In both embodiments, the distally increasing cross-section area of the infusion lumen 34 encourages flow of infusate fluids distally to contribute to an even distribution of infused fluids through the plurality of infusion ports $54_n$.

The resulting net cross-section area of the infusion lumen 34 within the improved infusion wire 10' and the distally increasing wire coil spacings allow a flow rate exceeding or comparable to the flow rate of the infusion wire 10 of the first embodiment and is relatively uniform along the infusion length. For example, the flow rates for room temperature water at 100 psi are specified for the following differing infusion lengths:

| | |
|---|---|
| 3.0 cm | 37.8 cc/min |
| 6.0 cm | 39.4 cc/min |
| 9.0 cm | 39.2 cc/min |
| 12.0 cm | 38.8 cc/min |

In use of the infusion wire 10', both slow drip, i.e., weeping, infusion and spray infusion may be effected. The improved infusion wire 10' is further specified to withstand pressures of up to 350 psi without bursting or tip leakage.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

PARTS LIST FOR FIGS. 1–11 infusion wire 10, 10'
proximal infusion wire portion 12
distal infusion wire portion 14
infusion wire proximal end 16
infusion wire distal end 18
luer connector housing 20
inner sheath 24, 24'
threaded male connector fitting 26
strain relief tube 28
inner sheath lumen 30
threaded female connector nut 32
infusion lumen 34
intermediate junction 36
keyed groove 38
wire coil 40
wire coil lumen 42
attachment ball 44
platinum marker tube 46
platinum marker wire coil 48
tubular outer sheath 50
outer sheath lumen 52
infusion port(s) $54_n$
elongated stiffening core wire 56
proximal core wire end 58
distal core wire end 60
hub member 62
outer surface 64
internal conduit 66
planar side walls 68, 70
flat, space wound coiled wire 72
outer polyimide sheath layer 74
inner polyimide sheath layer 76
proximal wire coil section 78
distal wire coil section 80
narrow coil spacing 82
intermediate coil spacing 84
wide coil spacing 86
proximal core wire portion 88
distal core wire portion 90
proximal core wire section 92
distal core wire section 94
proximal core wire transition zone 96
distal core wire transition zone 98
proximal core wire portion diameter 100
proximal core wire section diameter 102
distal core wire section diameter 104
proximal inner sheath section 106
distal inner sheath section 108

What is claimed is:

1. A flexible elongated medical infusion wire having a proximal infusion wire portion and a distal infusion wire portion enclosing an infusion lumen and extending between an infusion wire proximal end and an infusion wire distal end, the infusion wire adapted for introduction through a selected path in a patient's body to a site in a blood vessel or body cavity and for infusing infusate fluids into the blood vessel or body cavity, the infusion wire further comprising:

an inner sheath formed at least in part of a wire reinforced, polyimide tube providing resistance to collapse of the inner sheath through the proximal infusion wire portion in use of the infusion wire, the inner sheath having an inner sheath lumen formed therein, said inner sheath extending from said infusion wire proximal end and distally through said proximal infusion wire portion to an intermediate junction of said proximal infusion wire portion with said distal infusion wire portion;

a helically wound, distal wire coil extending between a distal wire coil proximal end and a distal wire coil distal end and having a distal coil lumen formed therein, said distal wire coil extending distally from said intermediate junction through said distal infusion wire portion to said infusion wire distal end, said wire coil having a proximal wire coil section and a distal wire coil section, said proximal wire coil section closely wound at a close coil winding pitch and said distal wire coil section space wound at a varying coil pitch to provide a distally increasing helical spacing between adjacent coil turns;

an outer sheath extending between said proximal infusion wire end and said distal infusion wire end having a sheath side wall enclosing an outer sheath lumen receiving said inner sheath in a proximal outer sheath portion thereof and receiving said wire coil in a distal outer sheath portion thereof such that said inner sheath lumen and said coil lumen are substantially co-axially aligned at said intermediate junction and define said infusion lumen;

a plurality of infusion ports formed through said outer sheath side wall that are spaced apart from one another and extend along said distal outer sheath portion for a defined infusion length thereof for allowing transmission of infusate fluids from said infusion lumen and through the helical spacing of said distal wire coil section and through said infusion ports to the exterior of said distal outer sheath portion;

an elongated stiffening core wire extending between a proximal core wire end and a distal core wire end comprising a proximal core wire portion positioned within said inner sheath lumen and extending therein from said proximal infusion wire end to said intermediate junction and a distal core wire portion positioned within said distal coil lumen and extending therein from said intermediate junction to said distal infusion wire end, said proximal core wire portion formed with a proximal core wire portion diameter smaller than the diameter of said inner sheath lumen thereby defining a proximal infusion lumen having a proximal infusion lumen cross-section area in said proximal infusion wire portion, said distal core wire portion further formed of a proximal core wire section and a distal core wire sections, said proximal core wire section formed with a proximal core wire section diameter smaller than the diameter of said distal coil lumen, and said distal core wire section formed with a distal core wire section diameter smaller than said proximal core wire section diameter, thereby providing a distal infusion lumen having a distally increasing distal infusion lumen cross-section area; and means engaging said proximal core wire end and the proximal ends of said outer sheath and said inner tubular sheath for allowing the infusion of the infusate fluid into the proximal infusion lumen at the infusion wire proximal end and transmission of the infusate fluid distally through said proximal infusion lumen to the distal infusion lumen, whereby the distally increasing cross-section area of the distal infusion lumen and the distally increasing helical spacing provide emission of the infusate fluid out of the plurality of infusion ports to the exterior of said distal outer sheath portion in a relatively uniform flow rate along the defined infusion length.

2. The infusion wire of claim 1, wherein:
said inner sheath comprises a proximal inner sheath section formed of said wire reinforced polyimide tube comprising a flattened wire that is space wound into a coiled wire and embedded within a polyimide material and a distal inner sheath section formed of polyimide tube.

3. The infusion wire of claim 1, wherein said core wire further comprises:
a proximal core wire transition zone extending between said proximal core wire portion and said proximal core wire section of said distal core wire portion tapered in cross-section to reduce the diameter of said core wire from said proximal core wire portion diameter to said proximal core wire section diameter, said proximal core wire transition zone and proximal core wire section dimensioned to resist bending force tending to kink said distal infusion wire portion distally to said intermediate junction.

4. The infusion wire of claim 3, wherein said core wire further comprises:
a distal core wire transition zone extending between said proximal core wire section and said distal core wire section tapered in cross-section to reduce the diameter of said core wire from said proximal core wire section diameter to said distal core wire section diameter, said distal core wire transition zone and distal core wire section dimensioned to allow a curvature to be formed in said distal infusion wire portion distally to said intermediate junction.

5. The infusion wire of claim 4, wherein:
said inner sheath comprises a proximal inner sheath section formed of said wire reinforced polyimide tube and a distal inner sheath section formed of polyimide tube.

6. The infusion wire of claim 1, wherein:
said inner sheath comprises a proximal inner sheath section formed of said wire reinforced polyimide tube and a distal inner sheath section formed of polyimide tube.

7. The infusion wire of any of the claims 1–6, further comprising:
means for attaching said distal core wire end to said distal wire coil distal end.

8. The infusion wire of any of the claims 1–6, further comprising:
radiopaque means disposed in coaxial alignment with said inner tubular sheath and said distal wire coil within said outer sheath lumen.

9. The infusion wire of any of the claims 1–6, further comprising:
a radiopaque wire coil having a plurality of spaced apart coil turns and a further inner coil lumen formed therein, said plurality of coil turns disposed within said helical spacing extending between a like plurality adjacent distal wire coil turns and maintained in coaxial alignment therewith within said outer sheath lumen such that said distal coil lumen and said further coil lumen are substantially co-axially aligned and define said infusion lumen.

10. A flexible elongated medical infusion wire having a proximal infusion wire portion and a distal infusion wire portion enclosing an infusion lumen and extending between an infusion wire proximal end and an infusion wire distal end, the infusion wire adapted for introduction through a selected path in a patient's body to a site in a blood vessel or body cavity and for infusing infusate fluids into the blood vessel or body cavity, the infusion wire further comprising:

an inner sheath formed of wire reinforced, polyimide tube providing resistance to collapse of the inner sheath and proximal infusion wire portion in use of the infusion wire, the inner sheath having an inner sheath lumen formed therein, said inner sheath extending from said infusion wire proximal end and distally through said proximal infusion wire portion to an intermediate junction of said proximal infusion wire portion with said distal infusion wire portion;

a helically wound, distal wire coil extending between a distal wire coil proximal end and a distal wire coil distal end and having a distal coil lumen formed therein, said distal wire coil extending distally from said intermediate junction through said distal infusion wire portion to said infusion wire distal end, said wire coil having a proximal wire coil section and a distal wire coil section, said proximal wire coil section closely wound at a close coil winding pitch and said distal wire coil section space wound at a varying coil pitch to provide a distally increasing coil spacing between adjacent coil turns;

an outer sheath extending between said proximal infusion wire end and said distal infusion wire end having a sheath side wall enclosing an outer sheath lumen receiving said inner sheath in a proximal outer sheath portion thereof and receiving said wire coil in a distal outer sheath portion thereof such that said inner sheath lumen and said coil lumen are substantially co-axially aligned at said intermediate junction and define said infusion lumen;

a plurality of infusion ports formed through said outer sheath wall that are spaced apart from one another and extend along said distal outer sheath portion for a defined infusion length thereof for allowing transmission of infusate fluids from said infusion lumen and through the helical spacing of said distal wire coil section and through said infusion ports to the exterior of said distal outer sheath portion, an elongated stiffening core wire extending between a proximal core wire end and a distal core wire end positioned within said infusion lumen to extend therein from said proximal infusion wire end to said distal infusion wire end, said core wire tapered in cross-section distally in said distal infusion wire portion thereby increasing the cross-section area of said infusion lumen distally; and means engaging said proximal core wire end and the proximal ends of said outer sheath and said inner tubular sheath for allowing the infusion of the infusate fluid into the infusion lumen at the infusion wire proximal end and transmission of the infusate fluid distally through said infusion lumen to the distal infusion wire portion, through the helical spacing and out of the plurality of infusion ports to the exterior of said distal outer sheath portion in a relatively uniform flow rate along the defined infusion length.

11. The infusion wire of claim 10, wherein:

said inner sheath is formed of a flattened wire that is space wound into a coiled wire and embedded within a polyimide material.

12. The infusion wire of claim 10, wherein:

said inner sheath is formed of a proximal inner sheath section having a proximal section formed of said wire reinforced polyimide tube and a distal inner sheath section of polyimide tube.

13. The infusion wire of claim 10, further comprising:

means for attaching said distal core wire end to said distal wire coil distal end.

14. The infusion wire of claim 13, wherein:

said inner sheath is formed of a proximal inner sheath section having a proximal section formed of said wire reinforced polyimide tube comprising a flattened wire that is space wound into a coiled wire and embedded within a polyimide material and a distal inner sheath section of polyimide tube.

15. The infusion wire of claim 10, wherein:

said inner sheath is formed of a proximal inner sheath section having a proximal section formed of said wire reinforced polyimide tube and a distal inner sheath section of polyimide tube.

16. A flexible elongated medical infusion wire having a proximal infusion wire portion and a distal infusion wire portion enclosing an infusion lumen and extending between an infusion wire proximal end and an infusion wire distal end, the infusion wire adapted for introduction through a selected path in a patient's body to a site in a blood vessel or body cavity and for infusing infusate fluids into the blood vessel or body cavity, said infusion wire further comprising:

an inner sheath having an inner sheath lumen formed therein, said inner sheath extending from said infusion wire proximal end and distally through said proximal infusion wire portion to an intermediate junction of said proximal infusion wire portion with said distal infusion wire portion;

a helically wound, distal wire coil extending between a distal wire coil proximal end and a distal wire coil distal end and having a distal coil lumen formed therein, said distal wire coil extending distally from said intermediate junction through said distal infusion wire portion to said infusion wire distal end, said wire coil having a proximal wire coil section and a distal wire coil section, said proximal wire coil section closely wound at a close coil winding pitch and said distal wire coil section space wound at a varying coil pitch to provide a distally increasing helical spacing between adjacent coil turns;

an outer sheath extending between said proximal infusion wire end and said distal infusion wire end having an outer sheath lumen formed therein for receiving said inner sheath in a proximal outer sheath portion thereof and for receiving said wire coil in a distal outer sheath portion thereof such that said inner sheath lumen and said coil lumen are substantially co-axially aligned at said intermediate junction and define said infusion lumen;

a plurality of infusion ports formed in said distal outer sheath portion that are spaced apart from one another and extend along said distal outer sheath portion thereof for a defined infusion length of said distal infusion wire portion, said infusion ports allowing emission of infusate fluids transmitted distally through said distal infusion lumen and through the helical spacing of said distal wire coil section through said plurality of infusion ports to the exterior of said distal outer sheath portion;

an elongated stiffening core wire extending between a proximal core wire end and a distal core wire end positioned within said infusion lumen to extend therein from said proximal infusion wire end to said distal infusion wire end, said core wire tapered in cross-section distally in said distal infusion wire portion thereby increasing the cross-section area of said infusion lumen distally; and means engaging said proximal core wire end and the proximal ends of said outer sheath and said inner tubular sheath for allowing the infusion of the infusate fluid into the infusion lumen at the infusion wire proximal end and transmission distally through said infusion lumen to the distal infusion wire portion, through the helical spacing and out of the plurality of infusion ports to the exterior of said distal outer sheath portion in a relatively uniform flow rate along the defined infusion length.

17. The infusion wire of claim 16, wherein said core wire further comprises:

a proximal core wire portion and a distal core wire portion, said proximal core wire portion formed with a proximal core wire portion diameter smaller than the diameter of said inner sheath lumen, said distal core wire portion further formed of a proximal core wire section and a distal core wire section, said proximal core wire section formed with a proximal core wire section diameter smaller than said proximal core wire portion diameter, and said distal core wire section formed with a distal core wire section diameter smaller than said proximal core wire section diameter, thereby increasing the cross-section area of said infusion lumen distally.

18. The infusion wire of claim 17, wherein said core wire further comprises:

a proximal core wire transition zone extending between said proximal core wire portion and said proximal core wire section of said distal core wire portion tapered in cross-section to reduce the diameter of said core wire from said proximal core wire portion diameter to said proximal core wire section diameter, said proximal core wire transition zone and proximal core wire section dimensioned to resist bending force tending to kink said distal infusion wire portion distally to said intermediate junction.

19. The infusion wire of claim 18, wherein said core wire further comprises:

a distal core wire transition zone extending between said proximal core wire section and said distal core wire section tapered in cross-section to reduce the diameter of said core wire from said proximal core wire section diameter to said distal core wire section diameter, said distal core wire transition zone and distal core wire section dimensioned to allow a curvature to be formed in said distal infusion wire portion distally to said intermediate junction.

20. The infusion wire of any of the claims 16–19, further comprising:

means for attaching said distal core wire end to said distal wire coil distal end.

21. A flexible elongated medical infusion wire having a proximal infusion wire portion and a distal infusion wire portion enclosing an infusion lumen and extending between an infusion wire proximal end and an infusion wire distal end, the infusion wire adapted for introduction through a selected path in a patient's body to a site in a blood vessel or body cavity and for infusing infusate fluids into the blood vessel or body cavity, the infusion wire further comprising:

an inner sheath having an inner sheath lumen formed therein, said inner sheath extending from said infusion wire proximal end and distally through said proximal infusion wire portion to an intermediate junction of said proximal infusion wire portion with said distal infusion wire portion;

a helically wound, distal wire coil extending between a distal wire coil proximal end and a distal wire coil distal end and having a distal coil lumen formed therein, said distal wire coil extending distally from said intermediate junction through said distal infusion wire portion to said infusion wire distal end, said wire coil having a proximal wire coil section and a distal wire coil section, said proximal wire coil section closely wound at a close coil winding pitch and said distal wire coil section space wound to provide a distally increasing helical coil spacing between adjacent coil turns;

an outer sheath extending between said proximal infusion wire end and said distal infusion wire end having a sheath side wall enclosing an outer sheath lumen receiving said inner sheath in a proximal outer sheath portion thereof and receiving said wire coil in a distal outer sheath portion thereof such that said inner sheath lumen and said coil lumen are substantially co-axially aligned at said intermediate junction and define said infusion lumen;

a plurality of infusion ports formed through said outer sheath side wall that are spaced apart from one another and extend along said distal outer sheath portion for a defined infusion length thereof for allowing transmission of infusate fluids from said infusion lumen and through the helical spacing of said distal wire coil section and through said infusion ports to the exterior of said distal outer sheath portion;

an elongated stiffening core wire extending between a proximal core wire end and a distal core wire end comprising a proximal core wire portion positioned within said inner sheath lumen and extending therein from said proximal infusion wire end to said intermediate junction and a distal core wire portion positioned within said distal coil lumen and extending therein from said intermediate junction to said distal infusion wire end, said proximal core wire portion formed with a proximal core wire portion diameter smaller than the diameter of said inner sheath lumen thereby defining a proximal infusion lumen having a proximal infusion lumen cross-section area in said proximal infusion wire portion, said distal core wire portion further formed of a proximal core wire section and a distal core wire section, said proximal core wire section formed with a proximal core wire section diameter smaller than the diameter of said distal coil lumen, and said distal core wire section formed with a distal core wire section diameter smaller than said proximal core wire section diameter, thereby providing a distal infusion lumen having a distally increasing distal infusion lumen cross-section area; and means engaging said proximal core wire end and the proximal ends of said outer sheath and said inner tubular sheath for allowing the infusion of the infusate fluid into the proximal infusion lumen at the infusion wire proximal end and transmission of the infusate fluid distally through said proximal infusion lumen to the distal infusion lumen, whereby the distally increasing cross-section area of the distal infusion lumen and the distally increasing helical spacing provide emission of the infusate fluid out of the plurality of infusion ports to the exterior of said distal outer sheath portion in a relatively uniform flow rate along the defined infusion length.

22. The infusion wire of claim 21, wherein said core wire further comprises:

a proximal core wire transition zone extending between said proximal core wire portion and said proximal core wire section of said distal core wire portion tapered in cross-section to reduce the diameter of said core wire from said proximal core wire portion diameter to said proximal core wire section diameter, said proximal core wire transition zone and proximal core wire section dimensioned to resist bending force tending to kink said distal infusion wire portion distally to said intermediate junction.

23. The infusion wire of claim 22, wherein said core wire further comprises:

a distal core wire transition zone extending between said proximal core wire section and said distal core wire section tapered in cross-section to reduce the diameter of said core wire from said proximal core wire section diameter to said distal core wire section diameter, said distal core wire transition zone and distal core wire section dimensioned allow a curvature to be formed in said distal infusion wire portion distally to said intermediate junction.

24. The infusion wire of any of the claims 21–23, further comprising:

means for attaching said distal core wire end to said distal wire coil distal end.

* * * * *